US008808719B1

(12) United States Patent
Flor-Weiler et al.

(10) Patent No.: US 8,808,719 B1

(45) Date of Patent: Aug. 19, 2014

(54) **USE OF *CHROMOBACTERIUM SUBSTUGAE* FORMULATIONS, COMPOSTIONS AND COMPOUNDS TO MODULATE CORNWORM ROOTWORM LARVAE INFESTATION**

(71) Applicant: Marrone Bio Innovations, Inc., Davis, CA (US)

(72) Inventors: Lina Flor-Weiler, Davis, IL (US); April Yang, Fremont, CA (US)

(73) Assignee: Marrone Bio Innovations, Inc., Davis, CA (US)

(*) Notice: Subject to any disclaimer, the term of this patent is extended or adjusted under 35 U.S.C. 154(b) by 0 days.

(21) Appl. No.: 13/842,981

(22) Filed: Mar. 15, 2013

(51) Int. Cl.
*A01N 25/00* (2006.01)
*A01N 63/00* (2006.01)

(52) U.S. Cl.
USPC .......................................... 424/405; 424/93.4

(58) Field of Classification Search
USPC ................................................ 424/93.4, 425
See application file for complete search history.

(56) References Cited

U.S. PATENT DOCUMENTS

| | | | | |
|---|---|---|---|---|
| 5,047,424 | A | 9/1991 | Puritch | |
| 5,428,175 | A | 6/1995 | Hoshino | |
| 6,077,860 | A | 6/2000 | Meunier | |
| 6,103,228 | A | 8/2000 | Heins | |
| 7,037,494 | B2 | 5/2006 | Mattingly | |
| 7,244,607 | B2 * | 7/2007 | Martin et al. | 435/252.1 |
| 7,901,914 | B2 | 3/2011 | Tan et al. | |
| 2006/0263368 | A1 | 11/2006 | Rosenblum et al. | |
| 2007/0172463 | A1 | 7/2007 | Martin | |
| 2009/0111759 | A1 | 4/2009 | Pedersen | |
| 2012/0100236 | A1 | 4/2012 | Asolkar | |

FOREIGN PATENT DOCUMENTS

| | | |
|---|---|---|
| KR | 10-2007-0088150 | 8/2007 |
| WO | WO 91/00012 | 1/1991 |
| WO | WO 01/74161 | 10/2001 |
| WO | WO 2004056960 | 7/2004 |
| WO | WO 2011/110932 | 9/2011 |
| WO | WO 2013/062977 | 5/2013 |

OTHER PUBLICATIONS

Martin et al., "Toxicity of *Chromobacterium subtsugae* to Southern green stink bug (Heteroptera: Pentatomidae and corn rootworm (Coleoptera: Chrysomelidae)," J Econ Entomol 100(3):680-684, 2007.*

Asolkar et al. "Daryamides A-C, Weakly Cytotoxic Polyketides from a Marine-Derived Actinomycete of the Genus Streptomyces Strain CNQ-085" J. Nat. Prod. 69:1756-1759. 2006.

Aspelin et al. "Pesticides Industry Sales and Usage, 1996 and 1997" U.S E.P.A. Publication 733-R-99-001. 1999.

Arena et al. "The Mechanism of Action of Avermectins in *Caenorhabditis elegans*: Correlation Between Activation of Glutamate-Sensitive Chloride Current, Membrane Binding and Biological Activity" Journal of Parasitology 81: 286-294. 1995.

Bakhetia et al. "RNA Interference of Dual Oxidase in the Plant Nematode *Meloidogyne incognita*" Molecular Plant-Microbe Interactions 18: 1099-1106. 2005.

(Continued)

*Primary Examiner* — Rosanne Kosson

(74) *Attorney, Agent, or Firm* — Ying-Horng Liu

(57) ABSTRACT

Provided is the use of or compositions or formulations comprising *Chromobacterium* species, filtrate, supernatant, extract, pesticidally active compound or metabolite derived therefrom as an insecticide, particularly against infestation of Corn Rootworm larvae.

5 Claims, 1 Drawing Sheet

(56) References Cited

OTHER PUBLICATIONS

Balibar et al. "In Vitro Biosynthesis of Violacein from L-Tryptophan by the Enzymes VioA-E from *Chromobacterium violaceum*" Biochemistry 45: 15444-15457. 2006.
Brazilian National Genome Project Consortium, "The Complete Genome Sequence of *Chromobacterium violaceum* Reveals Remarkable and Exploitable Bacterial Adaptability," Proc. Natl. Acad. Sci. 100(20):11660-11665. 2003.
Chalvet-Monfray et al. "Synergy Between Deltamethrin and Prochloraz in Bees: Modeling Approach" Environmental Toxicology and Chemistry 15(4): 525-534. 1996.
Chitwood. "Phytochemical Based Strategies for Nematode Control" Annual Review of Phytopathology 40: 221-249. 2002.
Chitwood. "Nematicides" In *Encyclopedia of Agrochemicals*, J. R. Plimmer (ed).New York, John Wiley & Sons. 3: 1104-1115. 2003.
Colby. "Calculating Synergistic and Antagonistic Responses of Herbicide Combinations" Weeds 15(1): 20-22. 1967.
Cronin et al. "Inhibition of Egg Hatch of the Potato Cyst Nematode Globodera Rostochiensis by Chitinase-Producing Bacteria" European Journal of Plant Pathology 103:433-440. 1997.
Durán et al. "Biosynthesis of a Trypanocide by *Chromobacterium violaceum*" World Journal of Microbiology and Biotechnology 10:686-690. 1994.
Dong et al. "Microbial Control of Plant-Parasitic Nematodes: A Five-Party Interaction" Plant Soil 288: 31-45. 2006.
Durán et al. "Violacein: Properties and Biological Activities" Biotechnol. Appl. Biochem. 48: 127-133. 2007.
Durán et al. "Potential Applications of Violacein: a Microbal Pigment" Med. Chem. Res. 21:1524-1532. 2012.
Farenhorst et al. "Synergy in Efficacy of Fungal Entomopathogens and Permethrin Against West African Insecticide-Resistant Anopheles Gambiae Mosquitoes" PLoS One 5(8): e12081. 2010.
Faske et al. "Sensitivity of Meloidogyne Incognita and Rotylenchulus Reniformis to Abamectin" Journal of Nematology 38: 240-244. 2006.
Guerena. "Nematode: Alternative Controls" from www.agrisk.umn.edu/cache/arl02971.htm, ATTRA Publication #IP287. 2006.
Hallmann et al. "Toxicity of Fungal Endophyte Secondary Metabolites to Plant-Parasitic Nematodes and Soil-Borne Pathogens" European Journal of Plant Pathology 102: 155-162. 1996.
Hasky-Gunther et al. "Resistance Against Potato Cyst Nematode Globodera Pallida Systemically Induced by the Rhizobacteria *Agrobacterium* Radiobacter(G12) and *Bacillus sphaericus* (B43)" Fundamentals of Applied Nematology 21: 511-517. 1998.
Hoshino et al. "Biosynthesis of Violacein: Origins of the Hydrogen, Nitrogen and Oxygen Atoms in the 2-Pyrrolidone Nucleus" Agric. Biol. Chem. 51: 2733-2741. 1987.
Hummelbrunner et al. "Acute, Sublethal, Antifeedant, and Synergistic Effects of Monoterpenoid Essential Oil Compounds on the Tobacco Cutworm, *Spodoptera litura* (Lep., Noctuidae)" J. Agric. Food Chem. 49(2): 715-720. 2001.
Hungria et al. "Genetic Characterization of *Chromobacterium* Isolates from Black Water Environments in the Brazilian Amazon" Lett. Appl. Microbiol. 41: 17-23. 2005.
Jaffee et al. "Susceptibility of Root-Knot and Cyst Nematodes to the Nematode-Trapping Fungi Monocrosporium Ellipsosporum and M. Cionopagum" Soil Biology and Biochemistry 27: 1083-1090. 1995.
Kämpfer et al. "*Chromobacterium piscinae* Sp. Nov. and *Chromobacterium pseudoviolaceum* Sp. Nov., from Environmental Samples" Int. J. Syst. Evol. Microbiol. 59: 2486-2490. 2009.
Kerry. "Exploitation of the Nematophagous Fungal Verticillium Chlamydosporium Goddard for the Biological Control of Root-Knot Nematodes (*Meloidogyne* Spp.)," In *Fungi as Biocontrol Agents: Progress, Problems and Potential*. T. M. Butt, C. Jackson and N. Magan (eds). New York, CAB International, p. 155-168. 2001.
Kirkegaard et al. "Biofumigation Potential of Brassicas" Plant and Soil 201: 71-89. 1998.
Koenning et al. "Survey of Crop Losses in Response to Phytoparasitic Nematodes in the United States for 1994" Supplement to the Journal of Nematology 31(4S): 587-618. 1999.
Kokalis-Burelle et al. "Allelochemicals as Biopesticides for Management of Plant-Parasitic Nematodes." In *Alleolochemicals: Biological Control of Plant Pathogens and Diseases*. Inderjit and K. G. Mukerji (eds). Netherlands, Springer: 15-29. 2006.
Krieg et al. "*Bacillus thuringiensis* var. tenebrionis: A New Pathotype Effective Against Larvae of Coleoptera," Z. Angew. Entomol. 96: 500-508. 1983. (English Abstract).
Martin et al."Bacterial Strains Lethal to Colorado Potato Beetle Larvae," Abstracts of the General Meeting of the American Society for Micorbiology 101:603. 2001.
Martin et al. "Survival of *Chromobacterium violaceum*, An Insect Pathogen Under Various Conditions," Abstracts of the General Meeting of the American Society for Microbiology 102:389-390. 2002.
Martin et al. "Characterization of *Chromobacterium* sp., a Purple Bacterium Toxic to Insects," Abstracts of the General Meeting of the American Society for Microbiology 103:Q-226. 2003.
Martin et al. "A Method to Detect Viable, Pigmented Insect Pathogens from Soil," Abstracts of the General Meeting of the American Society for Microbiology 103:Q-436. 2003.
Martin. "A Freeze-Dried Diet to Test Pathogens of Colorado Potato Beetle" Biological Control 29(1): 109-114. 2004.
Martin et al. "*Chromobacterium subtsugae* sp. nov., a Betaproteobacterium Toxic to Colorado Potato Beetle and Other Insect Pests" Int. J. Syst. Evol. Microbiol. 57: 993-999. 2007.
Martin et al. "Toxicity of *Chromobacterium subtsugae* to Southern Green Stink Bug (Heteroptera:Pentatomidae) and Corn Rootworm (Coleoptera:Chrysomelidae)" J. Econ. Entomol. 100: 680-684. 2007.
Mcclean et al. "Quorum Sensing and *Chromobacterium violaceum*: Exploitation of Violacein Production and Inhibition for the Detection of N-Acylhomoserine Lactones" Microbiology 143: 3703-3711. 1997.
Meyer et al. "Combinations of Biocontrol Agents for Management of Plant-Parasitic Nematodes and Soilborne Plant-Pathogenic Fungi" Journal of Nematology 34: 1-8. 2002.
Oka et al. "Nematicidal Activity of Essential Oils and their Components Against the Root-Knot Nematode" Phytopathology 90:710-715. 2000.
Oostendorp et al. "In-vitro Interrelationships Between Rhizosphere Bacteria and *Heterodera schachtii*" Reviews in Nematology 13: 269-274. 1990.
Quarles (ed.) "Directory of Least-Toxic Pest Control Products." The IPM Practitioner 26:17. 2005.
Roubtsova et al. "Effect of Broccoli (*Brassica oleracea*) Tissue, Incorporated at Different Depths in a Soil Column, on *Meloidogyne incognita*" Journal of Nematology 39: 111-117. 2007.
Ryan et al. "Divergent Pathways in the Biosynthesis of Bisindole Natural Products" Chem. Biol. 16: 351-364. 2009.
Sanchez, et al. "Reevaluation of the Violacein Biosynthetic Pathway and its Relationship to Indolocarbazole Biosynthesis" ChemBioChem 7, 1231-1240. 2006.
Sasser et al. "A World Perspective on Nematology: The Role of the Society" In *Vistas on Nematology*. J.A. Veech and D.W. Dickson (Eds.), Society of Nematologists, Hyattsville, MD. p. 7-14. 1987.
Saxena et al. "Bacterial Biocontrol Agents and their Role in Plant Disease Management." In *Biocontrol Potential and its Exploitation in Sustainable Agriculture. vol. 1: Crop Diseases, Weeds, and Nematodes*. R. R. Upadhaya,.K. G. Mekerji and B. P. Chamola (eds). New York, Kluwer Academic Plenum Publishers. 2000.
Shapiro-Ilan et al. "Effects of Combining Microbial and Chemical Insecticides on Mortality of the Pecan Weevil (Coleoptera: Curculionidae)" J. Econ. Entomol. 104(1): 14-20. 2011.
Siddiqui et al. "Biological Control of Plant Parasitic Nematodes by Fungi: a Review" Bioresource Technology 58: 229-239. 1996.
Siddiqui et al. "Role of Bacteria in the Management of Plant Parasitic Nematodes: a Review" Bioresource Technology 69: 167-179. 1999.
Siddiqui et al."Neem Allelopathy and the Root Knot Nematode" The IPM Practitioner 23:9-11. 2001.
Sikora et al. "Biological Control of Plant-Parasitic Nematodes with Plant-Health Promoting Rhizobacteria" In *Pest Management: Biologically Based Technologies*. Lumsden R.D., Vaughn J.L (eds). Pro-

(56) References Cited

OTHER PUBLICATIONS ceedings of Beltsville Symposium XVIII, Washington. American Chemical Society: 166-172. 1993.
Terefe et al. "Effect of a Formulation of *Bacillus* Firmus on Root-Knot Nematode *Meloidogyne incognita* Infestation and the Growth of Tomato Plants in the Greenhouse and Nursery" Journal of Invertebrate Pathology 100: 94-99. 2009.
Thompson et al. "Spinosad—a Case Study: An Example from a Natural Products Discovery Programme" Pest Manag. Sci. 56: 696-702. 2000.
Whitehead. "Plant-Parasitic Nematodes, Their Importance and Control," In *Plant Nematode Control*. Wallingford, UK, CAB International. p. 1-12, 1998.
Wirth et al. "Synergy Between Toxins of *Bacillus thuringiensis* subsp. Israelensis and *Bacillus Sphaericus*" J. Med. Entomol. 41: 935-941. 2004.
Young et al. "*Chromobacterium* Aquaticum sp. nov., Isolated from Spring Water Samples" Int. J. Syst. Evol. Microbiol. 58: 877-880. 2008.
Zeck. "A Rating Scheme for Field Evaluation of Root-Knot Nematode Infestations" Pflanzenschutznachrichten Bayer 24,1: 141-144. 1971.
Durán et al. "*Chromobacterium violaceum*: A Review of Pharmacological and Industrial Perspectives" Crit. Rev. Microbiol. 27: 201-222. 2001.
International Search Report and Written Opinion issued in PCT App. No. PCT/US2011/057541 dated Jun. 26, 2012.

* cited by examiner

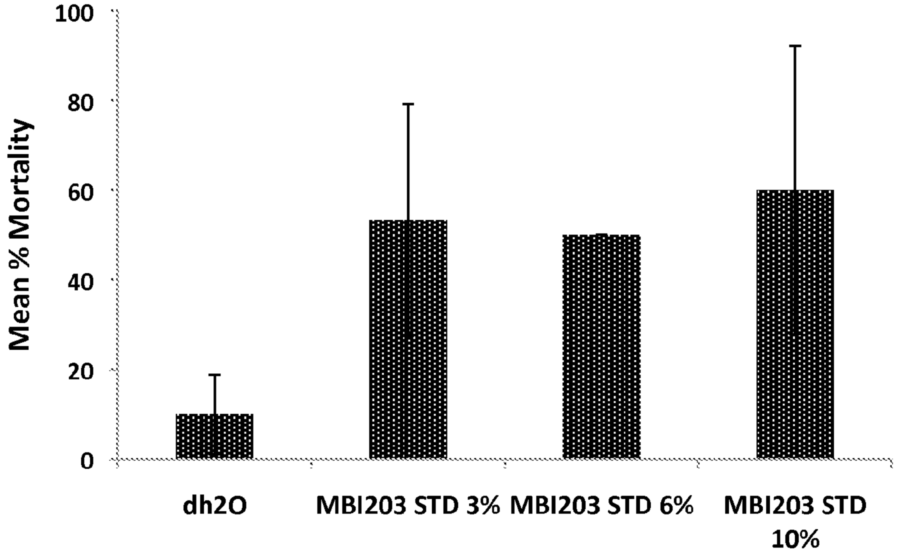
Mean % Mortality
100
80
60
40
20
0
dh2O
MBI203 STD 3%
MBI203 STD 6%
MBI203 STD 10%

USE OF *CHROMOBACTERIUM SUBSTUGAE* FORMULATIONS, COMPOSTIONS AND COMPOUNDS TO MODULATE CORNWORM ROOTWORM LARVAE INFESTATION

TECHNICAL FIELD

Provided is the use of or compositions or formulations comprising *Chromobacterium* species, filtrate, supernatant, extract, pesticidally active compound or metabolite derived therefrom as an insecticide, particularly against infestation of *Diabrotica* (Corn Rootworm) larvae.

BACKGROUND

In 2000, Dr. Martin and her coworkers at USDA isolated a purple-pigmented bacteria (PRAA4-1) from a forest soil in Maryland (Martin et al., 2007a). It is a facultatively aerobic, motile, Gram-negative betaproteobacterium with polar flagella. Colonies formed at 2-3 days on an L-agar plate at 25° C. are initially cream colored, gradually turning light to dark violet during the following 24 hours. Colonies of PRAA4-1 grow well on peptone based media with an optimum at 25° C., pH 6.5-8.0, and with 0-1.5% (w/v) NaCl (Martin et al., 2007a). This motile, Gram-negative, bacteria was identified as a new species of Chromobacteria, *Chromobacterium substsugae* sp. nov (Martin et al., 2007c). and or alternatively as *Chromobacterium substsugae* NRRL B-30655.

The effect of *Chromobacterium substsugae* NRRL B-30655 on insects does vary. It has been found to be toxic to Colorado Potato Beetle larvae but not to adults when these insects were fed a diet including *Chromobacterium substsugae* NRRL B-30655 (Martin, 2007b, 2007c). It was found to be toxic to adult southern green stink bugs but appeared to have a faster effect on males (Martin 2007c). For diamondback moth instar larvae fed a diet including *Chromobacterium substsugae* NRRL B-30655, the mortality was 90% in 7 days. None of the gypsy moth larvae died following treatment with NRRL B-30655, but the larvae which consumed NRRL B-30655 in their diet were 40% lighter than the controls. For mosquito larvae, there was no mortality at 48 hrs. although the larvae in the *B. thuringiensis* control were dead in 16 hrs.

With respect to Southern and Western Corn Rootworms, about 80% of both Southern and Western Corn Rootworm adults died when fed *Chromobacterium substsugae* NRRL B-30655 in a bait formulation; in other assays 100% mortality was reached after 120 hr. (Martin, 2007c). However, mortality in southern corn rootworm larvae was only found to be 40% when fed whole cultures. There was though a difference in the weight in larvae fed NRRL B-306555 as compared to the controls (Martin, 2007c).

US patent application publication no. US20120100236 also discloses compounds obtainable or derived from *Chromobacterium* species, more particularly, *Chromobacterium substugae*. In particular, PCT appln. no. PCT/US2012/061503 discloses the use of *Chromobacterium* species as an acaricide and insecticide, particularly against infestation of one or more pests belonging to the Acarina, Scarabeidae, Drosophilidae, Triozidae, Aphidae, Muscidae, Anthomyiidae or Tenebrionidae families.

SUMMARY

Provided is a method for modulating infestation of corn rootworm larvae in a location where modulation is desired comprising applying an amount of (a) a culture, suspension or whole cell broth comprising a strain of *Chromobacterium* sp., or supernatant, filtrate, cell fraction, extract and/or one or more compounds derived from said culture, suspension or whole cell broth and (b) optionally at least one of a carrier, diluent or adjuvant effective to modulate said infestation of corn rootworm larvae at said location. In a particular embodiment, the strain has the identifying characteristics of *Chromobacterium substugae* NRRL B-30655.

Infestation of *Diabrotica* (corn rootworm) larvae may be modulated by modulating mortality of corn rootworm larvae, specifically by modulating and particularly increasing or boosting mortality of corn rootworm larvae and/or by decreasing hatching rate of eggs laid and/or decreasing the number of eggs laid in a particular location.

BRIEF DESCRIPTION OF THE FIGURES

FIG. 1 shows the mean percent (%) mortality of corn rootworm first instar larvae on MBI-203 treated corn seedlings.

DETAILED DESCRIPTION OF THE PREFERRED EMBODIMENTS

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or culture broth, suspension or medium used to culture or grow said organism. A compound "derived from" or "obtainable from" means that a compound may be isolated from or produced by a cell culture, whole cell broth, suspension, filtrate, supernatant, fraction or extract.

As defined herein, "whole broth culture" or "whole cell broth" refers to a liquid culture containing both cells and media. If bacteria are grown on a plate, the cells can be harvested in water or other liquid, whole culture. The terms "whole broth culture" and "whole cell broth" are used interchangeably.

As defined herein, "supernatant" refers to the liquid remaining when cells grown in broth or are harvested in another liquid from an agar plate and are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer, organic solvent) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal activity.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods. A compound "derived from" a *Chromobacterium* species also encompasses a metabolite.

As defined herein, "carrier" is an inert, organic or inorganic material, with which the active ingredient is mixed or formulated to facilitate its application to plant or other object to be treated, or its storage, transport and/or handling.

The term "diluent" is intended to mean an aqueous or non-aqueous solution with the purpose of diluting the active ingredient.

As defined herein, "modulate", is used to mean to alter the amount or rate of pest infestation.

As defined herein, "pest infestation", is the presence of a pest in an amount that causes a harmful effect including a disease or infection in a host population or emergence of an undesired weed in a growth system.

As defined herein "pesticide", is a substance derived from a biological product or chemical substance that increase mortality or inhibit the growth rate of plant pests and includes but is not limited to nematicides, algaecides, herbicides, insecticides, plant fungicides, plant bactericides, and plant viricides.

Methods of Production

As noted above, the pesticide used in the method set forth herein may comprise or be derived from an organism having the identifying characteristics of a *Chromobacterium* species, more particularly, from an organism having the identifying characteristics of a strain of *Chromobacterium substugae*, more particularly from a strain of *Chromobacterium substugae* sp. nov. which may have the identifying characteristics of NRRL B-30655, or alternatively from any other microorganism. The methods comprise cultivating these organisms and obtaining the compounds and/or compositions of the present invention by isolating these compounds from the culture of these organisms.

In particular, the organisms are cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermenters performed in suitable medium and under conditions allowing cell growth. The cultivation may take place in suitable nutrient medium comprising carbon and nitrogen sources and inorganic salts, using procedures known in the art. Suitable media are available may be available from commercial sources or prepared according to published compositions.

After cultivation, the compounds, metabolites and/or compositions may be extracted from the culture broth. The extract may be fractionated by chromatography. Compounds used may be metabolites and in a specific embodiment may include but is not limited to compounds set forth in US Patent Application Publication No. US20120100236 and PCT appln. no. PCT/US2012/061503, the contents of both which are incorporated herein by reference.

Compositions

The substances set forth above used in the compositions and methods disclosed herein can be formulated in any manner. Non-limiting formulation examples include but are not limited to Emulsifiable concentrates (EC), Wettable powders (WP), soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), and Seed treatments etc. In any formulation described herein, percent of the active ingredient is within a range of 0.01% to 99.99%.

The compositions may be in the form of a liquid, gel or solid. Liquid compositions comprise pesticidal compounds derived from a *Chromobacterium* strain, e.g. a strain having the identifying characteristics of *Chromobacterium substugae* sp. Nov and more particularly, having the identifying characteristics of NRRL B-30655 (see U.S. Pat. No. 7,244,607).

A solid composition can be prepared by suspending a solid carrier in a solution of pesticidal compounds and drying the suspension under mild conditions, such as evaporation at room temperature or vacuum evaporation at 65° C. or lower.

A composition may comprise gel-encapsulated compounds derived from the *Chromobacterium* strain. Such gel-encapsulated materials can be prepared by mixing a gel-forming agent (e.g., gelatin, cellulose, or lignin) with a culture or suspension of live or inactivated *Chromobacterium*, or a cell-free filtrate or cell fraction of a *Chromobacterium* culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA Inerts List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition as set forth above also comprises a stabilizing agent, which stabilizes a biological pesticide composition against physical separation and loss of activity due to exposure to sunlight. This stabilizing agent may be a benzoic acid salt or lignin sulfonate salt.

The composition may as noted above, further comprise an insecticide. The insecticide may include but is not limited to avermectin, Bt, neem oil, spinosads, *Burkholderdia* sp. as set forth in US Patent Appln. Pub. No. 2011-0207604, entomopathogenic fungi such a *Beauveria bassiana* and chemical insecticides including but not limited to organochlorine compounds, organophosphorous compounds, carbamates, pyrethroids, and neonicotinoids.

Uses

The compositions, cultures and supernatants and pesticidal compounds set forth above may be used particularly to modulate infestation of corn rootworm larvae on a plant, plant seed, plant part, plant roots. seedling or substrate (e.g., soil, sand, loam, clay) for growing said plant, particularly a corn plant, cucurbits (e.g., cucumbers, melons, pumpkins, squash, gourds, etc.), wheat, barley, oats, rye, sorghum, beans and legumes, peas, potato, sweet potato, soy, oilseed rape, tomato, aubergine, lettuce, pepper, sunflower, and ornamental plants such as chrysanthemum as well as other plants such as red root pigweed (*Amaranthus retroflexus*), goosegrass (*Eleusine indica*) weeping lovegrass (*Eragrostis curvula*), sand lovegrass (*Eragrostis trichodes*), rhodes grass (*Chloris gayana*), shattercane (*Sorghum drummondii*), johnsongrass (*Sorghum halepense*), maize (*Zea mays*), sandbur (*Cenchrus tribuloides*), large crabgrass (*Digitaria sanquinalis*), barnyard grass, (*Echinochloa crus-galli*), woolly cupgrass (*Eriochloa villosa*), witchgrass (*Panicum capillare*), foxtail millet (*P. italicum*), Prosso millet (*P. miliaceum*), switchgrass (*P. virgatum*), giant foxtail (*Setaria faberi*), yellow foxtail (*S. pumila*), bristly foxtail (*S. vericillatta*), Green foxtail (*S. viridis*), texas panicum (*Urochloa texana*), Redtop (*Agrostis gigantean*), oat (*Avena sativa*), reed canarygrass (*Phalaris arundinacea*), downy brome (*Bromus tectorum*), Orchardgrass (*Dactylis glomerata*), western wheatgrass (*Pascopyrum smithii*), spring wheat "Russ" (*Triticum aestivum*)

It may be used to modulate members go the genus *Diabrotica* (rootworm) including *Diabrotica balteata* (banded cucumber beetle), *Diabrotica barberi* (northern corn rootworm), *Diabrotica beniensis, Diabrotica cristata, Diabrotica curvipustulata, Diabrotica dissimilis, Diabrotica elegantula, Diabrotica emorsitans, Diabrotica graminea, Diabrotica hispanolae, Diabrotica lemniscata, Diabrotica linsleyi, Diabrotica longicornis, Diabrotica milleri, Diabrotica nummularis, Diabrotica occlusa, Diabrotica porracea, Diabrotica scutellata, Diabrotica speciosa* (cucurbit beetle or chrysanthemum beetle), *Diabrotica tibialis, Diabrotica trifasciata, Diabrotica undecimpunctatahowardi* (southern corn rootworm, a.k.a spotted cucumber bettle), *Diabrotica undecimpunctata tenella* (western cucumber beetle), *Diabrotica undecimpunctata undecimpunctata* (western spotted cucumber beetle), *Diabrotica virgifera virgifera* (western corn rootworm), *Diabrotica virgifera zea* (Mexican corn rootworm), *Diabrotica viridula, Diabrotica significata* (three-spotted cucumber beetle)

Southern, Western or Northern Corn Rootworm larvae. In a particular embodiment, infestation of corn rootworm larvae is modulated by modulating mean mortality of said larvae at a particular location, particularly at least about 50% and more particularly at least about 60% within at least about three days following application of said compositions, cultures and supernatants and pesticidal compounds set forth above.

EXAMPLE

The composition and methods set forth above will be further illustrated in the following, non-limiting Examples. The examples are illustrative of various embodiments only and do not limit the claimed invention regarding the materials, conditions, weight ratios, process parameters and the like recited herein.

Methods

A bioassay set up was done to determine the effect of a formulation of *Chromobacterium substugae* sp. nov. (MBI-203) on Southern Corn Rootworm larvae. Newly hatched corn rootworm larvae were used in the bioassay.

Corn seeds were soaked in water overnight for germination. After soaking, the water-imbibed seeds were laid out in a tray lined with moistened paper towels (at least 4 layers of paper towels were used), with seeds spread evenly in the tray. The seeds were then covered with 2-3 layers of paper towels. The paper towel on top of corn seeds was moistened with water until paper towels are completely wet, just enough to not to flood the seeds with water. Seeds in wet paper towels were then covered with a plastic wrap to contain high humidity and kept at room temperature. The seeds were allowed to germinate for 2-3 days.

Bioassay setup was done using 100 mm×15 mm sterile plastic petri dishes. Petri dishes were lined with 4 layers of paper towels moistened with deionized water. Five germinated corn seedlings were selected and placed in petri dishes. Bioassay setup was done with 4 treatments; a) MBI 203 TGAI (technical grade of active ingredient) at 3% vol:vol concentration, b) MBI-203 TGAI (technical grade of active ingredient) at 6% vol:vol concentration, c) MBI-203 TGAI at 3% vol:vol concentration, and d) $dH_2O$ (negative control). Each treatment replicated three times. Petri dishes with corn seedlings were labeled according to treatment. Treatment of seedlings was done by spraying 1 mL of treatment solution on seedlings in each dish using a spray bottle. Spray application was done in fume hood and allowed to air dry. After drying, 10 first instar corn rootworm larvae were introduced to each dish with treated corn seedlings. The seedlings in each dish were covered with moist paper towel before covering with the dish cover. The dishes with corn rootworm larvae were kept at room temperature. Larval mortality was assessed 3 days post introduction to treated seedlings.

Results

The MBI 203 TGAI at different concentration affected corn rootworm larvae 3 days post exposure to treated corn seedlings. Corn rootworms were found susceptible to the product with a 60% mean mortality attained on corn seedlings treated with 10% MBI 203 TGAI. MBI 203 concentrations at 3% and 6% caused 53.3% and 50% mortality (FIG. 1). All treatments have showed 50% or more larval mortality after 3 days of exposure.

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

REFERENCES

Clark, TL and B E Hibbard. 2004. Comparison of Nonmaize Hosts to Support Western Corn Rootworm (Coleoptera: Chrysomelidae) Larval Biology. Environ. Entomol. 33(3): 681-689.

Martin, P. A. W., D. Gundersen-Rindal, et al. (2007a). "*Chromobacterium substugae* sp. nov., a betaproteobacterium toxic to Colorado potato beetle and other insect pests." *Int. J. Syst. Evol. Microbiol.* 57: 993-999.

Martin, P. A., A. D. S. Shropshire, et al., (2007b). "*Chromobacterium substugae* sp. nov for control of insect pests" U.S. Pat. No. 7,244,607 B2.

Martin, P. A. W., Hirose, E., and Aldrich, J. R. 2007c. "Toxicity of *Chromobacterium substugae* to southern green stink bug (Heteroptera:Pentatomidae) and corn rootworm (Coleoptera:Chrysomelidae)". *J. Econ. Entomol.* 100: 680-684.

Martin, P. A. W., Blackburn, M., et al. (2004), "Two New Bacterial Pathogens of Colorado Potato Beetle (Colorado: Chrysomelidae)", *J. Econ. Entomol.* 97:774-780 (2004).

What is claimed is:

1. A method for inhibiting infestation of *Diabrotica* (corn rootworm) larvae in a location where inhibition is desired comprising applying an amount of a composition comprising a culture, suspension or whole cell broth comprising a strain of *Chromobacterium* sp., or a supernatant, filtrate, or extract derived from said culture, suspension or whole cell broth effective to inhibit said infestation of corn rootworm larvae at said location by inducing mortality in at least 50% of said corn rootworm larvae in said location.

2. The method according to claim 1, wherein the location where inhibition is desired is on a plant, plant seed, plant roots, plant part, seedling or substrate for growing said plant.

3. The method according to claim 1, wherein said *Chromobacterium* sp. is *Chromobacterium subtsugae* sp. Nov strain.

4. The method according to claim 1 wherein said *Diabrotica* (corn rootworm) larvae are Southern Corn Rootworm larvae.

5. The method according to claim 1, which further comprises applying another insecticidal substance.

* * * * *